United States Patent
Grafton et al.

(10) Patent No.: US 8,012,172 B2
(45) Date of Patent: *Sep. 6, 2011

(54) HIGH STRENGTH SUTURE WITH COATING AND COLORED TRACE

(75) Inventors: R. Donald Grafton, Naples, FL (US); Reinhold Schmieding, Naples, FL (US)

(73) Assignee: Arthrex, Inc., Naples, FL (US)

(*) Notice: Subject to any disclaimer, the term of this patent is extended or adjusted under 35 U.S.C. 154(b) by 274 days.

This patent is subject to a terminal disclaimer.

(21) Appl. No.: 11/369,961

(22) Filed: Mar. 8, 2006

(65) Prior Publication Data

US 2006/0155329 A1    Jul. 13, 2006

Related U.S. Application Data

(60) Division of application No. 10/160,176, filed on Jun. 4, 2002, now Pat. No. 7,029,490, and a continuation-in-part of application No. 09/950,598, filed on Sep. 13, 2001, now Pat. No. 6,716,234.

(60) Provisional application No. 60/330,913, filed on Nov. 2, 2001, provisional application No. 60/350,040, filed on Jan. 23, 2002, provisional application No. 60/354,499, filed on Feb. 8, 2002.

(51) Int. Cl.
*A61B 17/04* (2006.01)

(52) U.S. Cl. ...................................................... 606/228

(58) Field of Classification Search ............... 606/228, 606/229, 230, 231
See application file for complete search history.

(56) References Cited

U.S. PATENT DOCUMENTS

| | | | |
|---|---|---|---|
| 2,909,177 A * | 10/1959 | Lieberman et al. | 606/231 |
| 3,187,752 A | 6/1965 | Glick | |
| 3,463,158 A | 8/1969 | Schmitt et al. | |
| 3,527,650 A | 9/1970 | Block | |
| 3,540,452 A * | 11/1970 | Langner et al. | 606/231 |
| 3,636,956 A | 1/1972 | Schneider | |
| 3,762,418 A * | 10/1973 | Wasson | 606/226 |
| 3,847,156 A * | 11/1974 | Trumble | 606/231 |
| 3,942,532 A | 3/1976 | Hunter et al. | |
| 3,949,755 A | 4/1976 | Vauquois | |
| 4,043,344 A | 8/1977 | Landi et al. | |

(Continued)

FOREIGN PATENT DOCUMENTS

EP     0 561 108 A2    9/1993

(Continued)

OTHER PUBLICATIONS

B. Cohan et al., An Evaluation of Ultrastrong Polyethylene Fiber as an Ophthalmic Suture, *Arch Opthalmol*, vol. 103, p. 1816-1821 (Dec. 1985).

*Primary Examiner* — Darwin P Erezo

(74) *Attorney, Agent, or Firm* — Dickstein Shapiro LLP

(57) ABSTRACT

A high strength abrasion resistant surgical suture material with improved tie down characteristics is color coded for visualization and identification purposes. The suture features a multifilament cover formed of strands of ultra high molecular weight long chain polyethylene braided with polyester, nylon or a bioabsorbable material. Selected nylon fibers in the cover are provided in a color contrasting with the other cover fibers to provide an identifiable trace. The cover surrounds a core formed of twisted strands of ultrahigh molecular weight polyethylene. The suture, provided in a #2 size, has the strength of #5 Ethibond, is ideally suited for most orthopedic procedures, and can be attached to a suture anchor or a curved needle.

3 Claims, 2 Drawing Sheets

U.S. PATENT DOCUMENTS

| | | | | |
|---|---|---|---|---|
| 4,047,533 A | | 9/1977 | Perciaccante et al. | |
| 4,052,988 A | | 10/1977 | Doddi et al. | |
| 4,141,087 A | | 2/1979 | Shalaby et al. | |
| 4,321,038 A | | 3/1982 | Porteous | |
| 4,344,908 A | | 8/1982 | Smith et al. | |
| 4,411,854 A | | 10/1983 | Maurer et al. | |
| 4,422,993 A | | 12/1983 | Smith et al. | |
| 4,430,383 A | | 2/1984 | Smith et al. | |
| 4,436,689 A | | 3/1984 | Smith et al. | |
| 4,470,941 A | | 9/1984 | Kurtz | |
| 4,543,286 A | | 9/1985 | Harpell et al. | |
| 4,563,392 A | * | 1/1986 | Harpell et al. | 428/394 |
| 4,610,688 A | | 9/1986 | Silverstrini | |
| 4,624,256 A | | 11/1986 | Messier et al. | |
| 4,668,717 A | | 5/1987 | Lemstra et al. | |
| 4,713,075 A | * | 12/1987 | Kurland | 128/898 |
| 4,792,336 A | * | 12/1988 | Hlavacek et al. | 623/13.18 |
| 4,946,467 A | * | 8/1990 | Ohi et al. | 606/228 |
| 4,959,069 A | | 9/1990 | Brennen et al. | |
| 4,979,956 A | | 12/1990 | Silverstrini | |
| 5,019,093 A | | 5/1991 | Kaplan et al. | |
| 5,067,538 A | | 11/1991 | Nelson et al. | |
| 5,116,360 A | | 5/1992 | Pinchuk et al. | |
| 5,120,802 A | | 6/1992 | Mares et al. | |
| 5,147,400 A | | 9/1992 | Kaplan et al. | |
| 5,217,495 A | * | 6/1993 | Kaplan et al. | 623/13.18 |
| 5,234,764 A | | 8/1993 | Nelson et al. | |
| 5,261,886 A | | 11/1993 | Chesterfield et al. | |
| 5,314,446 A | | 5/1994 | Hunter et al. | |
| 5,318,575 A | | 6/1994 | Chesterfield et al. | |
| 5,383,925 A | | 1/1995 | Schmitt | |
| 5,403,659 A | | 4/1995 | Nelson et al. | |
| 5,454,834 A | * | 10/1995 | Boebel et al. | 606/228 |
| 5,540,703 A | | 7/1996 | Barker, Jr. et al. | |
| 5,630,976 A | | 5/1997 | Nelson et al. | |
| 5,720,765 A | | 2/1998 | Thal | |
| 6,045,571 A | | 4/2000 | Hill et al. | |
| 6,063,105 A | | 5/2000 | Totakura | |
| 6,716,234 B2 | * | 4/2004 | Grafton et al. | 606/228 |
| 6,994,719 B2 | * | 2/2006 | Grafton | 606/228 |
| 7,029,490 B2 | * | 4/2006 | Grafton et al. | 606/228 |
| 7,329,271 B2 | * | 2/2008 | Koyfman et al. | 606/228 |
| 2004/0267313 A1 | | 12/2004 | Amery et al. | |
| 2005/0149118 A1 | | 7/2005 | Koyfman et al. | |

FOREIGN PATENT DOCUMENTS

| | | |
|---|---|---|
| GB | 2 218 312 A | 11/1989 |

* cited by examiner

HIGH STRENGTH SUTURE WITH COATING AND COLORED TRACE

CROSS-REFERENCE TO RELATED APPLICATIONS

This is a divisional of U.S. patent application Ser. No. 10/160,176, filed Jun. 4, 2002, now U.S. Pat. No. 7,029,490, which claims the benefit of U.S. provisional application Ser. No. 60/330,913 filed Nov. 2, 2001, U.S. provisional application Ser. No. 60/350,040, filed Jan. 23, 2002, and U.S. provisional application Ser. No. 60/354,499 filed Feb. 8, 2002, and which is a continuation-in-part of U.S. patent application Ser. No. 09/950,598, filed Sep. 13, 2001, now U.S. Pat. No. 6,716,234.

BACKGROUND OF THE INVENTION

1. Field of the Invention

The present invention relates to high strength surgical suture materials, and more particularly to braided suture blends of ultrahigh molecular weight polyethylene having coatings to improve handling, and colored strands for tracing and identifying the suture.

2. Description of the Related Art

Suture strength is an important consideration in any surgical suture material. One of the strongest materials currently formed into elongated strands is an ultrahigh molecular weight long chain polyethylene, typically used for fishing line and the like, which is sold under the trade names Dyneema or Spectra. This material is much stronger than ordinary surgical suture, however, it does not have acceptable knot tie down characteristics for use in surgical applications.

BRIEF SUMMARY OF THE INVENTION

The present invention advantageously provides a high strength surgical suture material with improved tie down characteristics. The suture features a braided cover made of a blend of ultrahigh molecular weight long chain polyethylene fiber and a fiber of one or more long chain synthetic polymers, preferably polyester. The polyethylene provides strength. The polyester provides improved tie down properties.

Handling properties of the high strength suture also are enhanced using various materials to coat the suture. In addition, strands of a contrasting color are added to the braided threads to enhance visibility. The colored strands preferably are dyed filaments of polyester or nylon.

In a preferred embodiment, the suture includes a multifilament cover formed of ultrahigh molecular weight polyethylene fiber braided with polyester and nylon fibers. The cover surrounds a fiber core substantially or entirely of ultrahigh molecular weight polyethylene. The core preferably comprises 3 strands of ultrahigh molecular weight polyethylene, twisted at about 3 to 6 twists per inch.

The cover preferably comprises 8 strands of ultrahigh molecular weight polyethylene braided with 6 strands of polyester and 2 strands of nylon, the nylon strands being provided in black or some other contrasting color as explained in greater detail below.

Ultrahigh molecular weight polyethylene fibers suitable for use in the present invention are marketed under the Dyneema trademark by Toyo Boseki Kabushiki Kaisha, and are produced in the U.S. by Honeywell under the trademark Spectra.

The suture of the present invention advantageously has the strength of Ethibond #5 suture, yet has the diameter, feel and tie ability of #2 suture. As a result, the suture of the present invention is ideal for most orthopedic procedures such as rotator cuff repair, achilles tendon repair, patellar tendon repair, ACL/PCL reconstruction, hip and shoulder reconstruction procedures, and replacement for suture used in or with suture anchors.

The suture can be uncoated, or coated with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the braid, knot security, or abrasion resistance, for example.

As an added advantage, as mentioned above, all or some of the nylon fibers (or the polyester fibers) in the cover are provided in a contrasting color for visibility and identification purposes. A few trace threads having a contrasting color, preferably of a readily dyed fiber such as polyester or nylon, in the cover aid surgeons in identifying the travel direction of the suture during surgery, particularly during arthroscopic operations. Providing the trace threads in a regularly repeating pattern is particularly useful, allowing the surgeon to distinguish different ends of lengths of suture, and determine the direction of travel of a moving length of suture. Of the more easily dyed fibers, nylon is preferred in that it accepts dye readily. Polyester fibers are stronger, but do not take up dye as easily as nylon.

Other features and advantages of the present invention will become apparent from the following description of the invention which refers to the accompanying drawings.

DETAILED DESCRIPTION OF THE INVENTION

Figure 1:
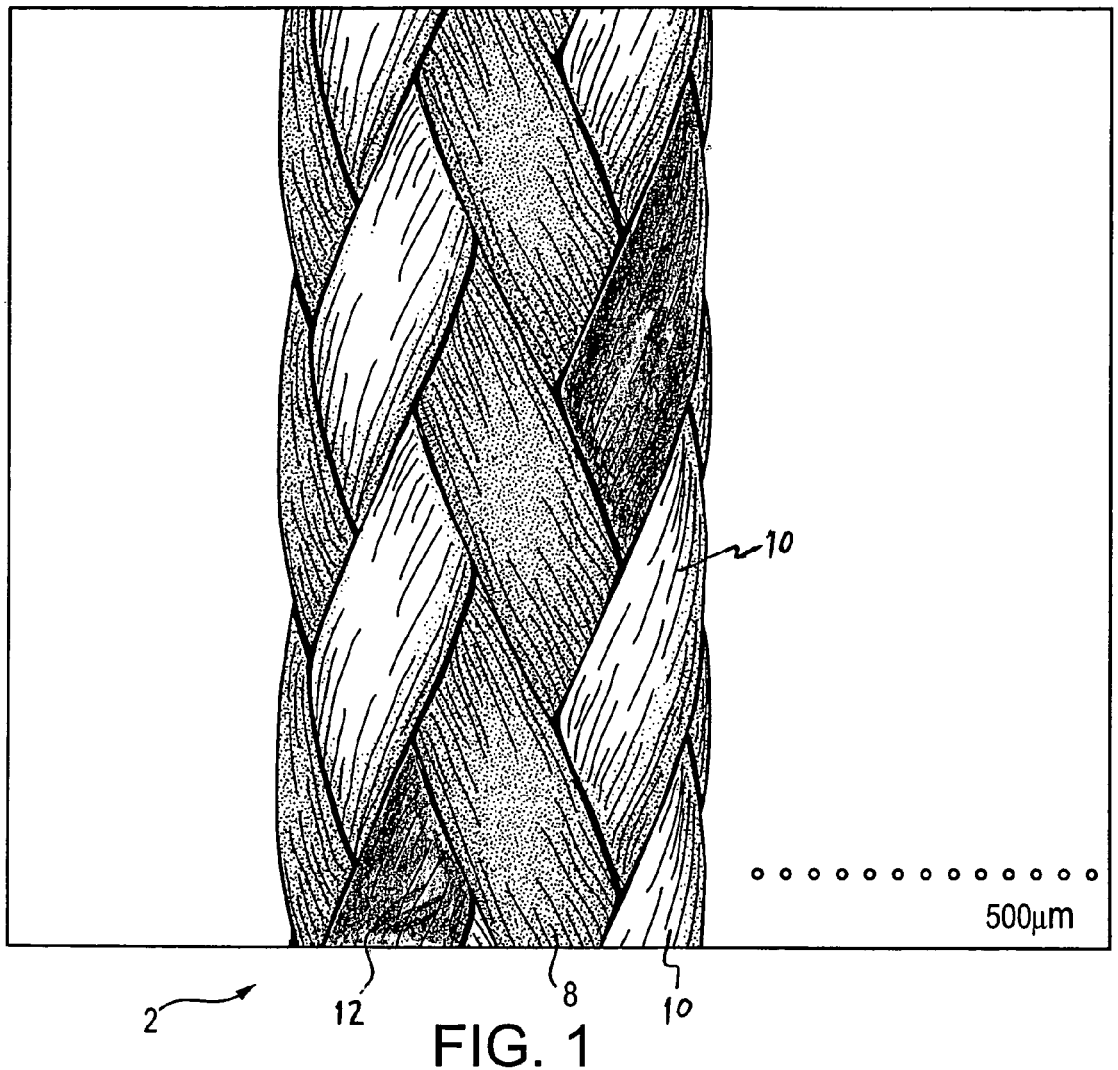
FIG. 1 is a copy of a scanning electron micrograph of a length of suture according to the present invention.
Figure 2:
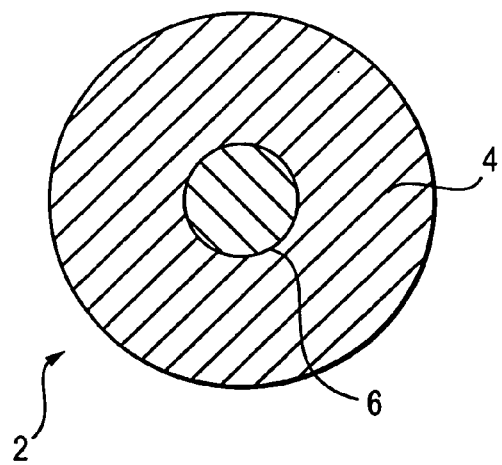
FIG. 2 is a schematic cross section of a length of suture according to the present invention.

Referring to FIG. 1, a scanning electron micrograph of a length of suture 2 according to the present invention is shown. Suture 2 is made up of a cover 4 and a core 6 surrounded by the cover. See FIG. 2. Strands of ultrahigh molecular weight polyethylene (UHMWPE) 8, sold under the tradename Spectra or Dyneema, and strands of polyester 10 and 12 are braided together to form the cover 4. Core 6 is formed of twisted strands of UHMWPE.

UHMWPE strands 8 are substantially translucent or colorless. The majority of the polyester strands 10 are white (undyed), with one or more additional polyester or nylon strands 12 having a contrasting color provide a trace in the suture. Due to the transparent nature of the UHMWPE, the suture takes on the color of strands 10 and 12, and thus appears to be white with a trace in the contrasting color. In accordance with the present invention, trace strands 12 are preferably provided in black. The black trace assists the surgeon in differentiating between suture strands with the trace and suture strands without the trace. The trace also assists the surgeon in identifying whether the suture is moving.

Details of the present invention will be described further below in connection with the following examples:

Example: USP Size 5 (EP Size 7)

Made on a 16 carrier Hobourns machine, the yarns used in the braided cover are Honeywell Spectra 2000, polyester type 712, and nylon. The cover is formed using eight strands of 144 decitex Spectra per carrier, braided with six strands of 100 decitex polyester, and two strands of colored nylon. The core is formed of three carriers of 144 decitex Spectra braided at three to six twists per inch.

The example set forth above is for size 5 suture. In the making of various sizes of the inventive suture, different decitex values and different PPI settings can be used to achieve the required size and strength needed. In addition, smaller sizes may require manufacture on 12 carrier machines, for example. The very smallest sizes preferably are made without a core. Overall, the suture may range from 5% to 90% ultrahigh molecular weight polymer (preferably at least 40% of the fibers are ultrahigh molecular weight polymer), with the balance formed of polyester and/or nylon. The core preferably comprises 18% or greater of the total amount of filament.

The suture preferably is coated with wax (beeswax, petroleum wax, polyethylene wax, or others), silicone (Dow Corning silicone fluid 202A or others), silicone rubbers (Nusil Med 2245, Nusil Med 2174 with a bonding catalyst, or others) PTFE (Teflon, Hostaflon, or others), PBA (polybutylate acid), ethyl cellulose (Filodel) or other coatings, to improve lubricity of the braid, knot security, or abrasion resistance, for example.

The ultra high molecular weight (UHMW) polymer component of the present invention provides strength, and the polyester component is provided to improve tie ability and tie down characteristics. However, it has been found that the UHMW polymer provides an unexpected advantage of acting as a cushion for the polyester fibers, which are relatively hard and tend to damage each other. The UHMW polymer prevents breakage by reducing damage to the polyester when the suture is subjected to stress.

According to an alternative embodiment of the present invention, a partially bioabsorbable suture is provided by blending a high strength material, such as UHMWPE fibers, with a bioabsorbable material, such as PLLA or one of the other polylactides, for example. Accordingly, a suture made with about 10% Spectra or Dyneema blended with absorbable fibers would provide greater strength than existing bioabsorbable suture with less stretch. Over time, 90% or more of the suture would absorb, leaving only a very small remnant of the knot. The absorbable suture can include coatings and colored traces as noted above for nonabsorbable suture.

Figure 3:
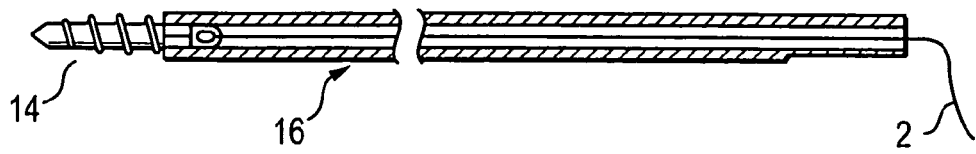
FIG. 3 is an illustration of the suture of the present invention attached to a suture anchor.
Figure 4A:
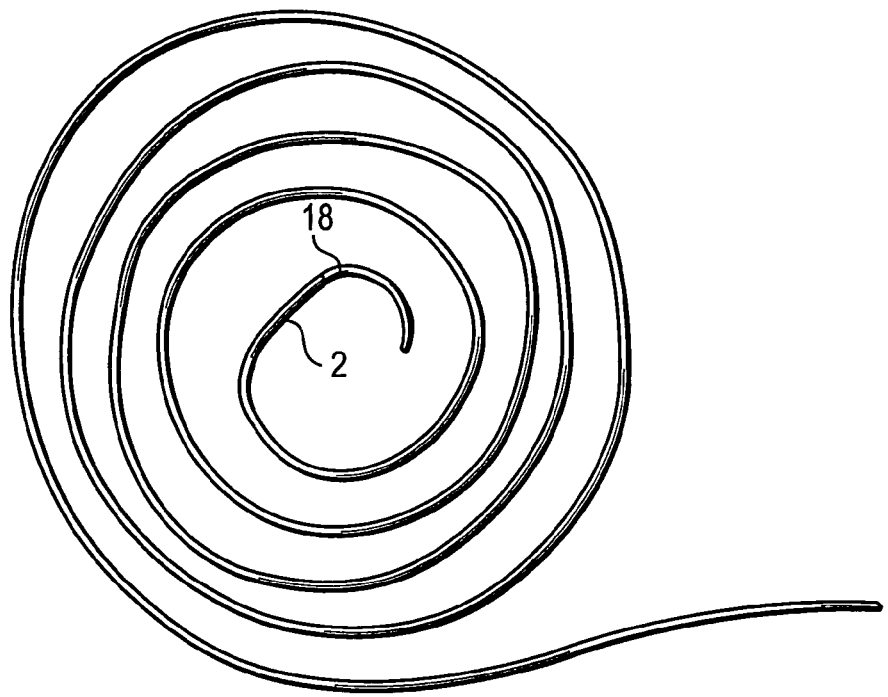
FIGS. 4A and 4B show the suture of the present invention attached to a half round, tapered needle.
Figure 4B:
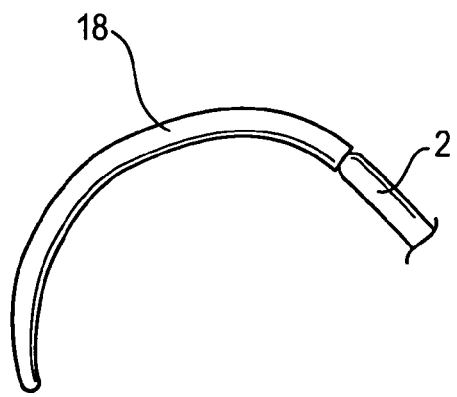

In one method of using the suture of the present invention, the suture 2 is attached to a suture anchor 14 as shown in FIG. 3 (prepackaged sterile with an inserter 16), or is attached at one or both ends to a half round, tapered needle 18 as shown in FIGS. 4A and 4B.

As set forth in Example 1 as described above, one or more strands of a fiber in the blend can be provided in pre-dyed colors, e.g., black, to provide a trace. The trace threads enhance the ability to visually detect suture motion and the ability to differentiate between colored and uncolored suture strands.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A suture strand suitable for use as a suture or ligature comprising:
   a sheath including fibers of ultrahigh molecular weight polyethylene braided with fibers of one or more long chain synthetic polymers other than ultrahigh molecular weight polyethylene,
   wherein the sheath further comprises at least one fiber provided with a color contrasting with the fibers of ultrahigh molecular weight polyethylene and the fibers of one or more long chain synthetic polymers, to provide an identifiable trace; and
   a core of twisted fibers of ultrahigh molecular weight polyethylene surrounded by the sheath.

2. A suture strand as in claim 1, wherein the at least one fiber provided with a color contrasting with fibers of ultrahigh molecular weight polyethylene and fibers of one or more long chain synthetic polymers is a dyed filament of polyester or nylon.

3. A suture strand suitable for use as a suture or ligature comprising:
   a first plurality of fibers comprising ultrahigh molecular weight polyethylene;
   a second plurality of fibers comprising a first long chain synthetic polymer other than ultrahigh molecular weight polyethylene; and
   a third plurality of fibers comprising dyed filaments of polyester or nylon,
   wherein the first plurality of fibers, the second plurality of fibers, and the third plurality of fibers are braided to form a sheath, and
   wherein the third plurality of fibers is provided with a color contrasting with the first plurality of fibers and the second plurality of fibers to provide an identifiable trace; and
   a core of twisted fibers of ultrahigh molecular weight polyethylene surrounded by the sheath.

* * * * *